US006274751B1

(12) United States Patent
Tacconi

(10) Patent No.: US 6,274,751 B1
(45) Date of Patent: Aug. 14, 2001

(54) WAX ESTERS ENRICHED IN ω-3 UNSATURATED FATTY ACIDS, THEIR PREPARATION AND THEIR USE

(75) Inventor: Maria Teresa Tacconi, Milan (IT)

(73) Assignee: Prime European Therapeuticals S.p.A.

( * ) Notice: Subject to any disclaimer, the term of this patent is extended or adjusted under 35 U.S.C. 154(b) by 0 days.

(21) Appl. No.: 09/445,419

(22) PCT Filed: Jun. 9, 1998

(86) PCT No.: PCT/EP98/03466

§ 371 Date: Mar. 14, 2000

§ 102(e) Date: Mar. 14, 2000

(87) PCT Pub. No.: WO98/56883

PCT Pub. Date: Dec. 17, 1998

(30) Foreign Application Priority Data

Jun. 11, 1997 (IT) .............................................. MI97A1369

(51) Int. Cl.$^7$ ................................................... C07C 57/00
(52) U.S. Cl. ........................... 554/224; 514/558; 514/560
(58) Field of Search .............................. 554/224; 514/558, 514/560

(56) References Cited

U.S. PATENT DOCUMENTS 5,463,143    10/1995    Singleton .

FOREIGN PATENT DOCUMENTS 90 04013    4/1990    (WO) .
92 22631    12/1992    (WO) .

OTHER PUBLICATIONS

Takagi T et al.: "Gas chromatographic resolution of polyunsaturated Wax esters based on their degree of unsaturation on silar 10C." Journal of Chromatographic Science, vol. 15, No. ¾, 1997, pp. 121–124, XP002083464 Dep. Of Chem., Fac. Of Fisheries, Hokkaido Univ., Hakodate, Japan see p. 121, col. 1; table 1.

Database WPI section Ch, Week 9551 Derwent Publications, Ltd., London, GB: Class B05, AN 95–397103 XP002083466 & JP 07 267898 A (Nisshin Flour Milling C0), Oct. 17, 1995 see abstract.

Garcia T et al: "Enzymatic synthesis of an analogue of jojoba oil: optimization by statistical analysis." Enzyme and Microbial Technology, vol. 15, No. 7, 1993, pp. 607–611, XP002083465 Correspondence (Reprint) address, J. Aracil, Dep. Of Chem. Eng., Fac of Chem., Complutense Univ., 28040 Madrid, Spain see p. 607–608.

*Primary Examiner*—Deborah D. Carr
(74) *Attorney, Agent, or Firm*—Nixon & Vanderhye

(57) ABSTRACT

This invention refers to wax esters enriched in ω-3 unsaturated fatty acids, to the procedure to obtain them, to their peculiar biochemical behavior which enables them to be used as drug and food additives, and to formulations which contain them for both pharmaceutical and dietetic-alimentary purposes.

7 Claims, No Drawings

WAX ESTERS ENRICHED IN ω-3 UNSATURATED FATTY ACIDS, THEIR PREPARATION AND THEIR USE

This applicatioin is a 371 of PCT/EP98/03466 filed Jun. 9, 1998.

This invention refers to wax esters enriched in ω-3 unsaturated fatty acids, to the procedure to obtain them, to their peculiar biochemical behaviour which enables them to be used as drug and food additives, and to formulations which contain them for both pharmaceutical and dietetic-alimentary purposes.

The name "wax" usually means a wide class of lipids, which are characterized more according to their physical feature than according to their chemical structure. Generally, a material is classified as a wax when it looks like honeycomb material.

On the contrary, from a strictly chemical point of view, waxes are particular carboxylic esters (wax esters). Namely, they are esters of long chain aliphatic acids (fatty acids) with long chain aliphatic alcohols. Both acids and alcohols can be either saturated or unsaturated. A full description of nature and characteristics of wax esters can be found in a review by P. E. Kolattukudy, "Chemistry and Biochemistry of Natural Waxes", Elsevier (1976), Amsterdam.

The starting material to be used in the preparation of products herein described is a mixture of esters enriched in ω-3 unsaturated fatty acids. This mixture is usually obtained by current industrial procedures from natural sources such as fish oil, containing a relatively high amount of polyunsaturated ω-3 fatty acids, such as EPA (eicosapentaenoic acid) and DHA (docosahexaenoic acid). In a common procedure, fish oil triglycerides are split by treatment with low boiling alcohols in the presence of a catalyst. After removing glycerol, esters thus obtained are further enriched in ω-3 unsaturated fatty acids by some techniques, such as distillation and urea fractionation.

Methyl and ethyl esters, enriched in EPA and DHA, along with natural or synthetical triglycerides, and free fatty acids, also enriched in EPA and DHA, have been the forms so far available for material enriched in ω-3 polyunsaturated acid, to be used as both pharmaceuticals and food integrators.

These forms have severe drawbacks, mainly due to their tendency to oxidation. These products go easily rancid when exposed to air. Oxidation by-products, even at a low content, render the main material stenching, irritant and disgusting, so that this cannot be easily handled and utilized.

From a technological standpoint, moreover, polyunsaturated fatty acids, their glycerides, and their esters with low boiling alcohols are thick oily liquids, so they are hard to formulate. The best solution so far used is to formulate them in soft jelly capsules, but also this expedient is not able to cancel inconveniences such as burping after ingestion.

Surprisingly, we have found that wax esters herein described can easily override these difficulties. Products herein described are easily handled since they are solid and less prone to oxidation. Nevertheless, the biological properties remain the same as in the case of all those oily derivatives mentioned before. Surprisingly, as a matter of fact, we have discovered that wax esters enriched in ω-3 polyunsaturated fatty acids are much more readily absorbed and metabolized than wax esters naturally encountered, characterized by a low contents in ω-3 fatty acids.

Products herein described are solid waxy materials, so that oxidation is limited to the only surface layer. Therefore, they can be formulated in several ways, preserving their biological and organoleptic properties.

Beneficial effects of ω-3 fatty acids, particularly of EPA and DHA, are well known for pathologies affecting the cardio-circulatory system (thrombosis, atherosclerosis, platelet hyperaggregation, hyperlipidhemia, hypercholesterolhemia), as well as for pathologies affecting the immune system, in inflammatory states, and in tumors. Moreover, the effects of lack of dietary DHA have been described (Tacconi M. T., Lligona L., Salmona M., Pitsikas M., and Algeri S., Neurobiol. of Aging, 12:55–59, 1990).

This invention concerns therefore also the use of wax esters herein described in the preparation of drugs which can conveniently used in the aforementioned pathologies, as well as in the preparation of dietetic and alimentary formulations.

Wax esters herein described are prepared from a mixture of esters of free fatty acids enriched in polyunsaturated fatty acids, where the alcohol moiety is usually methyl or ethyl alcohol, or, more generally, a low boiling alcohol. This mixture is reacted with one or more alcohols via a transesterification reaction, provided that these alcohols are the same ones found in natural wax esters, according to the following scheme:

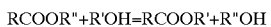

where
R: residue of an ω-3 unsaturated fatty acid,
R": methyl, ethyl, or a low boiling alcohol residue,
R':residue of an alcohol contained in natural wax esters.

For R, EPA and DHA residues are preferred. For R", methyl and ethyl are preferred. Finally, for R', residues of saturated alcohols are preferred, with a number of carbon atoms ranging from 12 and 40. Another preferred alcohol is oleyl alcohol.

The aforementioned scheme is not restrictive, since a mixture of esters RCOOR" can be simultaneously reacted with a mixture of alcohols R'OH, provided that, as stated before, the mixture represented by the formula RCOOR" is enriched in ω-3 unsaturated fatty acids, i.e., as an example, when RCOOR" represents the esters of EPA and DHA, these are contained in this mixture in percentage higher than 18% and 12% respectively, corresponding to the percentages of these two acids usually found in natural products.

Optimally, the reaction is performed starting from nearly stoichiometric amount of the reactants, and it is catalyzed by bases, according to procedures usually adopted for transesterifications. The product is obtained with the highest yield when low boiling alcohol R"OH is removed as a reaction product by distillation under reduced pressure.

After completion, the reaction mixture is treated with hot water containing small amounts of an acid, preferably citric acid, in order to quench and remove the catalyst, along with small traces of soap formed during the reaction. Further addition of hot water separates the wax ester as a melted liquid phase, which is allowed to separate and to solidify.

Wax esters described by this invention can be recrystallized in small white needle-shaped crystals. They can also be purified without any crystallization, simply by repeating the washing of the oily phase with some more water and citric acid. The product thus obtained can undergo a final treatment of deodorization, in order to remove by-products from oxidation, according to procedures usually used in alimentary oil technology.

According to the procedure thus described, the content of ω-3 unsaturated fatty acids in the final wax ester is the same as in the starting mixture of esters, as shown by the analysis of the acidic moiety obtained by hydrolysis of wax esters.

Transesterification reaction is the best suited procedure in order to obtain wax esters highly enriched in polyunsaturated fatty acids, but also other reactions can give the same products, starting both from esters enriched in polyunsaturated acids and from free fatty acids obtained by hydrolizing these esters. Some of these reactions can be mentioned, such as direct esterification of free fatty acids with alcohols, treatment of alcohols with reactive derivatives of acids, such as anhydrides, chlorides, isopropenyl esters, and so on, interesterification of either methyl or ethyl esters of fatty acids with either acetic or propionic esters of long chain alcohols.

Wax esters herein described are more stable toward air oxidation than the starting esters, as shown by the parallel determination of peroxide number, made at increasing times, of a sample of ethyl ester enriched in EPA and DHA and of the corresponding wax ester, when both samples were allowed to stand in an open vessel. After one week of exposure to air, peroxide number was increased from five to seven times more in the case of ethyl esters than in the case of wax esters; values were corrected on the basis of the actual weight of polyunsaturated fatty acid in the molecular formula of ethyl esters and of wax esters.

Similar results were obtained by monitoring the formation of formaldehyde as an oxidative by-product. Tests were performed according to Wilbur et al., Arch. Biochem. Biophys, 24:305,1949 as modified by Kikugawa et al. Anal. Biochem. 202:249, 1992 and they are reported in Table 1.

TABLE 1

Peroxidability of wax esters (200 mg) in vitro in comparison with same amounts of fish oil.

| Time after incubation | Wax esters | Fish oil absorbance (thiobarbituric acid reaction substances, TBARS, malondialdehyde units) |
|---|---|---|
| day 1 | 0.160 | 1.295 |
| day 2 | 0.323 | 1.996 |
| day 3 | 2.362 | 5.081 |

As to absorption and biotransformation of wax esters described by this invention, it has been found that these compounds are well absorbed and that they are actually metabolized, contrary to what described in the case of natural wax esters, which are not enriched in polyunsaturated fatty acids.

Digestibility of the products described by this invention was tested in in vitro experiments. After digestion with pancreas lipase, the hydrolysis of wax esters was monitored on the basis of formation of both the alcoholic and the acidic moieties. As a reference, jojoba oil was used, which is a natural oil containing an acid moiety where monounsaturated fatty acid are in the majority, and an alcoholic moiety containing prevailingly saturated chains. Thin layer chromatographic analysis clearly showed that wax esters enriched in $\omega$-3 unsaturated fatty acids were nearly completely hydrolyzed into their constituents already after 5 hours, whereas jojoba oil was nearly unreacted.

In vivo tests were performed on rats treated with a single dose of 5 g/kg of wax esters (acute treatment). Animals were killed 6 and 16 hours after the treatment. Results are reported in Tables 2 and 3.

Table 2 shows that plasma triglycerides are raised, in comparison with untreated animals, at both times after the treatment. Table 3 clearly shows that the plasma of treated animals was noticeably enriched in EPA and DHA 6 hours after the treatment, in comparison with untreated animals. No effect is visible after 16 hours from the treatment, probably because the rapid metabolism of lipids.

A protocol was also applied in order to study the effects of a chronic treatment. With a dose of 0.3 g/kg repeated for 15 days, no change in the weight of animals was noticed. Food consumption slightly decreased, whereas intestinal transit was not altered, as shown by Table 4. These results are in sharp contrast with results described in the case of natural waxes, where polyunsaturated acids are not major constituents of the acidic moiety (see the review quoted above, by P. E. Rolattukudy). In vivo tests are in agreement with in vitro results and all of them reinforce the evidence that enrichment of wax esters in $\omega$-3 unsaturated acids results in complete absorption and digestibility.

TABLE 2

Effect of an acute treatment with wax esters (5 g/kg, oral) on plasma lipids of rats

| | Time after treatment (h) | mg/dl ± SD | |
|---|---|---|---|
| | | Cholesterol | Triglycerides |
| Control | — | 64.7 ± 1.5 | 82.2 ± 5.5 |
| Wax esters | 6 | 60.0 ± 10.7 | 99.2 ± 6.9 |
| Wax esters | 16 | 68.9 ± 2.2 | 129.0 ± 5.3 |

TABLE 3

Effect of an acute treatment with wax esters (5 g/kg, oral) on the rat plasma content in fatty acids.

| Fatty acid | Main plasma fatty acids (moles %) | | |
|---|---|---|---|
| | Control | 6 hours after treatment | 16 hours after treatment |
| 12:0 | 0.2 | 0.2 | 0.2 |
| 14:0 | 0.5 | 0.3 | 0.5 |
| 15:0 | 0.3 | 0.2 | 0.5 |
| 16:0 | 21.0 | 13.6 | 20.4 |
| 18:0 | 13.7 | 12.6 | 8.8 |
| 18:1 | 14.9 | 8.1 | 14.2 |
| 18:2$\omega$3 | 25.4 | 18.3 | 32.5 |
| 18:3$\omega$3 | 1.7 | 1.1 | 2.1 |
| 20:2 | 0.1 | 1.0 | 0.8 |
| 20:3$\omega$6 | 0.5 | 0.5 | 0.8 |
| 20:4$\omega$6 | 9.7 | 13.4 | 6.3 |
| 20:5$\omega$3 (EPA) | 2.3 | 6.1 | 2.4 |
| 22:2 | 1.5 | 5.9 | 1.1 |
| 22:4 | 0.4 | 4.6 | 1.8 |
| 22:5$\omega$3 | 1.7 | 4.5 | 1.4 |
| 22:6$\omega$3 (DHA) | 4.7 | 7.0 | 2.6 |
| total $\omega$6 | 37.0 | 42.2 | 41.7 |
| total $\omega$3 | 10.4 | 18.7 | 8.5 |

TABLE 4

Effect of a subchronic treatment with wax ester (0.3 g/kg each day, for 15 days) on body weight, food consumption, and intestinal transit of rats.

| | (g ± SD) | | Food consumption | |
|---|---|---|---|---|
| | Initial body weight | Final body weight | Intestinal g/rat/day | transit % |
| Control | 174 ± 6.5 | 261 ± 4.0 | 31.0 | 48.0 |
| Wax esters | 173 ± 4.0 | 261 ± 5.6 | 27.3 | 52.6 |

As a conclusion, studies both in vivo and in vitro show the efficacy of the products described by this invention as a source of $\omega$-3 unsaturated fatty acids, as good as other products presently on the market. In addition, contrary with what met in the case of current products, these new products offer many advantages from a technological and formulative point of view.

Some formulative aspects, which concern only the products herein described, deserve some mention. For instance, wax esters can be sprayed in melted form and injected into cold water, where droplets of the product solidify in the form of small spheres with a prefixed radium. The procedure can be performed with water treated with salt and natural fragrances, in order to obtain synthetic caviar.

As an alternative, wax esters can be absorbed onto a solid matrix (flour, bran, granules, and so on) in order to obtain foods enriched in ω-3 unsaturated fatty acids.

In the pharmaceutical field, products described by this invention can be formulated using conventional excipients and techniques, such as described in "Remington's Pharmaceutical Sciences Handbook" Mack Publishing Company, New York, USA.

Therefore, this invention concerns also dietetic and pharmaceutical formulations containing wax esters enriched in ω-3 unsaturated fatty acids which can be obtained according to the procedures herein described.

The following examples, reporting the preparation of some wax esters enriched in ω-3 unsaturated fatty acids, explain the invention in better details.

EXAMPLE 1

25 gr of an enriched fish oil ester (saponification value= 170 mg KOH/gr, average molecular weight 330, EPA 33%, DHA 22% as from gaschromatographic area percent analysis) was mixed with 25 gr of behenyl alcohol (molecular weight 326). The mixture was treated with 0.3 gr of sodium methoxide and the flask was connected to a vacuum pump (40 mbar). Temperature was raised up to 120° C. The stirred mixture darkened, as ethanol started boiling at ca. 80° C. A temperature of 120° C. was maintained for half an hour. During this time, ethanol evolution almost ceased. The mixture was then cooled at 40° C., then the vacuum was removed by filling the flask with nitrogen. The liquid mixture was poured into a 1% aqueous solution of citric acid (200 ml) stirred under nitrogen at room temperature. Stirring was continued for five minutes at room temperature, then the mixture, still stirred, was cooled down to 5° C., whereby crystallization occurred. The solid material was filtered under vacuum, washed with water on the filter, and recrystallized from 400 ml of acetone. After cooling the mixture at —10° C. for one hour, the whitish crystalline product was filtered under vacuum and dried under reduced pressure overnight at room temperature. Yield: 42.5 gr (89%). The product gives a clean spot in TLC (silica gel plates, eluting system; n-hexane-ethyl ether 9:1, $R_f$=0.87, whereas $R_f$ of the starting ethyl ester=0.75, $R_f$ of behenyl alcohol=0.11). The melting point of the wax was 47° C.

EXAMPLE 2

The same ethyl ester of example 1 (33 gr) was reacted with 27 gr of stearyl alcohol (molecular weight 270). Reaction conditions were the same as for example 1. Yield: 43.5 gr (67.5%), after crystallization from 200 ml of acetone. A clear spot in TLC was detected (silica gel, m-hexane-ethyl ether 49:1; $R_f$=0.23). By superimposing this product with product of example 1, no separation can be observed. Melting point: 39° C.

EXAMPLE 3

25 gr of an ethyl ester enriched in EPA (74% EPA), with no DHA, (saponification value: 170, average molecular weight 330) were reacted with 25 gr of behenyl alcohol. Reaction conditions were the same as for example 1. The product obtained from water was not completely soluble even in large amounts of hot acetone, so it was filtered as it was a melted phase through a paper filter and dried under reduced pressure. Yield: 39.4 gr (82.7%): Melting point: 40° C.

EXAMPLE 4

25 gr of ethyl ester (the same as in Example 1) were reacted with 16.2 gr of 1-tetradecanol (molecular weight 214). Reaction conditions were the same as for example 1. After pouring the mixture into acidic water, the oily phase was washed twice at 45° C. with 100 ml of water. After separation, the oily phase was then dried under reduced pressure. Yield: 35 gr (90%). Melting point: 23° C. Thin layer chromatography showed a neat spot, with the same $R_f$ of the products of examples 1, 2, and 3.

EXAMPLE 5

33 gr of the same ethyl ester of example 1 (33% EPA, 22% DHA) were reacted by the same procedure of Example 1 with 24 gr of 1 hexadecanol (cetyl alcohol). The solid filtered from water at 3° C. was stirred in 50 ml of cold acetone (at −10° C.) for half an hour, then it was filtered under vacuum and dried under reduced pressure. Yield 47 gr (89%). Melting point 31° C.

EXAMPLE 6

33 gr of the same ethyl ester of example 1 were reacted with 29 gr of 1-eicosanol. After the same procedure and the same work up of example 1, 42 gr of wax ester were obtained (75%). Melting point 43° C.

EXAMPLE 7

The same preparation described in Example 2 was repeated. Crystallization from acetone was omitted, but the raw product obtained after separation of the melted wax from hot water was washed again by the same procedure. A product was obtained, having the same melting point and the same purity as the one described in Example 2. The yield was raised to 96%.

All samples (Examples 1–7) were subjected to hydrolysis according to the conditions described for the analysis of natural wax esters (Linskens, H. J. and Jackson, I. J., Essential Oils and Waxes, Springler Verlag, Berlin (1991)), followed by the proper work up and analysis of the composition of the free fatty acid moiety. Analyses showed the same EPA and DHA content in the wax esters as in the esters utilized as a starting material.

EXAMPLE 8

Digestibility test. The effect of pancreas lipase on wax esters has been verified according to the method by Neumann (U. Neumann, P. Kaspar, and J. Ziegenborn, "Methods in Enzymatic Analysis", Bergmayer HV, 1984, vol.4, pp.34–36). 800 mg of wax esters enriched in ω-3 polyunsaturated fatty acids, and, in parallel for a comparison, 800 mg of jojoba oil were incubated in a Tris buffer 0.125 M , pH 9.2, containing human pancreas lipase, colipase, and deoxycholic acid for different times at 37° C. After extraction of lipids, portions of organic phases containing lipids were dried and laid down on a silica gel TLC plate with concentration band. Plates were eluted with n-hexane-ethyl ether-acetic acid 80:20:1. Spot were visualized by exposure both to iodine and to sprayed sulphuric acid.

What is claimed is:

1. A composition of wax esters of ω-3 polyunsaturated fatty acids having a content of acyl residues of DHA and/or EPA higher than 12% and 18%, respectively.

2. A composition according to claim 1, in which the alcoholic moiety of the wax esters is selected from the group consisting of behenyl, stearyl, tetradec-1-yl, cetyl, eicos-1-yl, oleyl alcohol.

3. A composition according to claim 1, used as a medicament.

4. A composition according to claim 3, used in the treatment of cardio-circulatory diseases, thrombosis, platelet hyperaggregation, hyperlipidemia, hypercholesterolemia, inflammation, cancer, diseases of the immune system.

5. The composition of claim 1 as dietary-alimentary integrator.

6. Dietary-alimentary integrators containing the composition of claim 1.

7. Dietary-alimentary integrators according to claim 6, in the form of microspheres or absorbed onto a solid matrix used as food.

* * * * *